United States Patent [19]

Grozinger

[11] Patent Number: 5,616,717
[45] Date of Patent: Apr. 1, 1997

[54] PROCESS FOR THE PREPARATION OF PURE ENANTIOMERS OF 1-(2-PYRIDYL)-2-CYCLOHEXYLETHYLAMINE

[75] Inventor: Karl G. Grozinger, Ridgefield, Conn.

[73] Assignee: Boehringer Ingelheim Pharmaceuticals, Inc., Ridgefield, Conn.

[21] Appl. No.: 425,526

[22] Filed: Apr. 20, 1995

[51] Int. Cl.$^6$ .................................................. C07D 211/26
[52] U.S. Cl. ............................................................ 546/329
[58] Field of Search ............................................. 546/329

[56] References Cited

U.S. PATENT DOCUMENTS 5,296,486  3/1994  Lazer et al. ............................... 514/333

OTHER PUBLICATIONS

M. Aiqiao et al., "Asymmetric Synthesis XV: Enantioselective Syntheses of (R) or (S)-alpha-substituted-(2-pyridyl)-methylamines Via Chiral Pinanone Ketimine Template", Synth. Commun., 21(21), pp. 2207–2212 (1990).

E.S. Lazer et al., "Benzoxazolmines and Benzothiazolamines: Potent Enantioselective Inhibitors of Leukotriene Biosynthesis with a Novel Mechanism of Action", J. Med. Chem., 37(7), pp. 913–923 (1994).

L.A. Paquette, "Encylopedia of Reagents for Organic Synthesis, vol. 1", John Wiley & Sons, New York, pp. 708–709 (1995).

W. Yuliang et al., "Solid–Liquid Phase Transfer Catalytic Synthesis VII: The Synthesis of Alpha–substituted–2–pyridylmethylamine Via the Alkylation of Benzaldehyde Imine", Synth. Commun., 22(2), pp. 265–269 (1992).

E. Eliel, "Stereochemistry of Carbon Compounds", McGraw–Hill Book Co., New York, pp. 49–55 (1962).

P. Newman, "Optical Resolution Procedures for Chemical Compounds", vol. 1, Optical Resolution Information Center, Manhattan College, Riverdale, NY, pp. 2,11 and 64–65, (1978).

*Primary Examiner*—D. R. Wilson
*Attorney, Agent, or Firm*—Robert P. Raymond; Wendy E. Rieder; Mary-Ellen M. Devlin

[57] ABSTRACT

Racemic mixtures of 1-(S,R)-(2-pyridyl)-2-cyclohexylethylamine are separated into (+)-(S)-1-(2-pyridyl)-2-cyclohexylethylamine or (–)-(R)-1-(2-pyridyl)-2-cyclohexylethylamine by admixture with (+)- or (–)-3-bromocamphor-8-sulfonic acid. 1-(S)-(2-pyridyl)-2-cyclohexylethylamine is an intermediate in the preparation of leukotriene biosynthesis inhibitors.

2 Claims, No Drawings

PROCESS FOR THE PREPARATION OF PURE ENANTIOMERS OF 1-(2-PYRIDYL)-2-CYCLOHEXYLETHYLAMINE

This invention relates to the preparation of racemic mixtures of 1-(2-pyridyl)-2-cyclohexylethylamine and in particular the separation of (+)-(S)-1-(2-pyridyl)-2-cyclohexylethylamine or (−)-(R)-1-(2-pyridyl)-2-cyclohexylethylamine from these mixtures. 1-(2-pyridyl)-2-cyclohexylethylamine is an intermediate in the preparation of leukotriene biosynthesis inhibitors such as those described in E. S. Lazer et al. U.S. Pat. No. 5,296,486, issued Mar. 22, 1994.

BACKGROUND OF THE INVENTION

The preparation of racemic 1-(2-pyridyl)-2-cyclohexylethyl amine is described by P. L. Pickard and T. L. Tolbert, (Journal of Organic Chemistry 26, 4886, 1961) in a method which utilizes 2-cyanopyridine and an organometallic reagent such as cyclohexylmethylmagnesium bromide to form a kerimine intermediate which is reduced in situ. This procedure uses a Grignard reaction and anhydrous solvents. In an alternate process alkylation using a phase transfer catalyst has been described by J. March in "Advanced Organic Chemistry" Third Edition, 417, (1985). For other examples, see Fraser, Banville and Dhawan, J. A. C. S., 100, 7999, (1978); Corey and Enders, Chem. Ber. 111, 1337, (1978) and Asai, Aoyana and Shirori, Synthesis 811, (1980). In addition, Y. Wang et at. teach a process for preparing substituted-2-pyridyl methyl amines by condensing 2-pyridylamine with benzaldehyde followed by alkylation with an alkyl halide in the presence of tetrabutylammonium bromide (Synthetic Communications, 22(2), 265–269,1992). Each of these processes produce racemic mixtures of pyridyl cyclohexylalkylamine. However, efficient methods for separating the mixtures to recover the desired isomer have not been previously available. U.S. Pat. No. 5,296,486 describes the separation of racemic 1-(2-pyridyl)-2-cyclohexylethylamine via a diastereomeric amide. This procedure requires three extra steps and involves column chromatography which makes the method expensive in large scale production.

BRIEF DESCRIPTION OF THE INVENTION

Now it has been found that racemic mixtures of 1-(2-pyridyl)-2-cyclohexylethylamine can be readily produced and the racemates efficiently separated in a process for producing (+)-S or(−)-R-1-(2-pyridyl)-2-cyclohexylethylamine which comprises:

(a) reacting 2-aminomethylpyridine with an aromatic aldehyde or a ketone followed by the reaction with a cyclohexylmethyl halide to produce 1-(S,R)-(2-pyridyl)-2-cyclohexylethylamine, (b) admixing 1-(S,R)-(2-pyridyl)-2-cyclohexylethylamine with (+) or (−)-3-bromocamphor-8-sulfonic acid to produce a crystalline addition product, and, (c) admixing ammonium hydroxide with the crystalline addition product to recover (+)-S or (−)-R-1-(2-pyridyl)-2-cyclohexylethylamine.

DETAILED DESCRIPTION OF THE INVENTION

In the novel process of the present invention 2-aminomethyl pyridines are employed as one of the starting materials.

In one embodiment of the process of the invention the 2-aminomethylpyridine is condensed with an aromatic aldehyde or ketone to produce a Schiff's base. Any aldehyde or ketone used to prepare Schiff's bases may be employed. Preferably a broad group of aromatic aldehydes can be used including, for example, benzaldehyde, salicylaldehyde, 3,5-dichlorosalicylaldehyde, p-nitrobenzaldehyde and 2-pyridine carboxaldehyde or ketones such as benzophenone, substituted benzophenones, or acetophenone. Reaction conditions for the condensation are those commonly used in the formation of Schiff bases. The Schiff base produced is then reacted with a cyclohexylalkyl halide such as cyclohexylmethyl bromide. The alkylated Schiff's base is hydrolyzed in situ to produce a racemic mixture of a 1-(R,S)-(2-pyridyl)-2-cyclohexylalkylamine.

A phase transfer catalyst may also be employed in the alkylation reaction, i.e. a quaternary ammonium compound such as tetrabutyl ammonium iodide. The reaction mixture additionally may contain a base such as an alkali metal hydroxide with sodium hydroxide or potassium hydroxide being preferred. Also present in the reaction mixture may be solvents and other additives which are known to be used in alkylation reactions.

The separation of the racemates in the novel process of the present invention is effectively accomplished using an enantiomeric form of 3-bromo-camphor-8-sulfonic acid (BCSA) as the resolving agent. The resolution is carded out by adding a suspension of BCSA to a solution of the racemic mixture of 1-(R,S)-(2-pyridyl)-2-cyclohexylalkylamine and producing a crystalline addition product. To obtain optical purity, the pyridylamine(R or S)-BCSA salt is crystallized from an organic solvent such as isopropanol.

To produce, for example, the crystals of the 1-(S)-(2-pyridyl) cyclohexylalkylamine(+)-BCSA salt are treated with a base such as ammonium hydroxide to recover the desired 1-(S)-(2-pyridyl)-2-cyclohexylalkyl amine in high yields. Further amounts of the selected optical isomer can be obtained by treatment of the solution from crystallization with addtitonal BCSA.

The novel process of the present invention produces the desired isomer while avoiding the protection of the amine group required by some prior processes. Protection of the amine group requires extra stages, requires the use of expensive and/or hazardous materials, and requires the use of chromatography for purification. The novel process of the present invention avoids these extra steps, the use of expensive and hazardous materials and does not require chromatography for purification. Further, the process is highly suitable for large scale production.

The process of the present invention can be employed in the production of various substituted 2-benzoxazoles, 2-benzothiazoles, 2-oxazolopyridines and 2-thiazolopyridines, which compounds have the ability, inter alia, to inhibit leukotriene biosynthesis. Such compounds have the general formula:

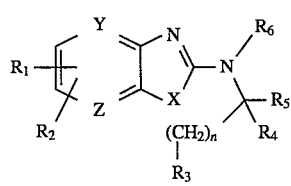

Formula I wherein:
X is O or S;
Y is C or N;
Z is C or N;

$R_1$ and $R_2$ are each, independent of one another, hydrogen; $C_1$-$C_6$ alkyl; halo; $CF_3$;

nitrile; $C_1$-$C_6$ alkoxy;

$R_3$ is cyclohexyl;

$R_4$ is a 2-, 3- or 4-pyridyl group;

$R_5$ and $R_6$ are independently of each other hydrogen or methyl; and n is an integer 0, 1 or 2.

The preferred compounds for inhibition of leukotriene biosynthesis are those wherein the $R_1$ substitutent is in the 5-position and is an $C_1$-$C_3$ alkyl group or halogen, $R_4$ is 2-pyridyl, the $R_5$ and $R_6$ substitutents are each hydrogen and n is 1.

The leukotriene-inhibiting compounds may be prepared by methods and processes known in the art and published in the literature such as U.S. Pat. No. 5,296,486 previously cited and which in its entirety is incorporated by reference. For example, compounds may be prepared by reaction of the pure enantiomer of 1-(2-pyridyl)-2-cyclohexylalkyl amine with an appropriately substituted 2-chlorobenzoxazole, 2-chlorobenzothiazole, 2-chlorooxazolopyridine or 2-chlorothiazolopyridine of the following formula:

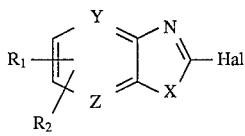

Formula 2 wherein:

X is O or S;

Y is C or N;

Z is C or N;

$R_1$ and $R_2$ are each, independent of one another, hydrogen; $C_1$-$C_6$ alkyl;

halo; $CF_3$; nitrile; $C_1$-$C_6$ alkoxy; and

Hal is Cl, Br, or I.

The reaction may occur in an inert solvent, such as methylene chloride, toluene, acetonitrile, diisopropyl ether or DMSO, and with a basic catalyst, such as triethylamine or an alkali metal hydroxide (eg. NaOH or KOH). The optimum choice of both solvent and catalyst will depend upon the nature of the reactants, as a person skilled in the art would recognize.

The following examples are illustrative of the present invention. These examples, however, are not to be construed as limiting the scope of the present invention, which scope is defined in the claims which follow.

EXAMPLE 1

Preparation of Racemic 1-(pyridyl)-2-cyclohexylethylamine

To a refluxed stirred mixture of 1.34 kg (55.8 moles) of magnesium in 6 L of t-butylmethyl ether (MTBE) and 4 g (0.016 moles) of iodine, a solution of 10 kg (55.9 moles) cyclohexylmethyl bromide in 22 L (MTBE) was added slowly. After approximately 10% to 25% of the solution was added, heating was discontinued and the remainder of the solution was added at a rate to maintain refluxing temperature. After the addition, the reaction was refluxed for an additional 24 hrs, then cooled to 0° to 5° C. and 3.903 kg (37.1 moles) of 2-cyanopyridine in 22 L MTBE was added at 0°–10° C. After the addition, the greenish thick suspension was stirred without cooling for 18–24 hrs. The Grignard reaction mixture was transferred with stirring to 40 L of methanol at 10° to 15° C. To the clear solution was added 1.4 kg (36.8 moles) of sodium borohydride. The mixture was stirred at room temperature 18 hrs., then quenched by the addition of 16 L of water and 36 L of 4N hydrochloric acid. The organic solvents were removed under vacuum and the remaining aqueous solution was washed twice with 6 L of methylene chloride. The aqueous phase was basified with 15 L of ammonium hydroxide solution and extracted three times with 10 L of methylene chloride. The methylene chloride was dried over 6.5 kg of sodium sulfate and concentrated to yield 5.645 kg (75%) of 1-(R,S)-(2-pyridyl)-2-cyclohexylethylamine.

EXAMPLE 2

Under a nitrogen atmosphere, 1.365 kg (12.86 moles) of benzaldehyde was added with stirring and cooling to 1.39 kg (12.86 moles) of 2-(aminomethyl)pyridine maintaining the temperature <50° C. After stirring for 2–4 hours, the mixture was diluted with 13 L of t-butylmethyl ether (MTBE). To the clear solution was added 1.05 kg (27.72 moles) sodium hydroxide (flakes) and 2.375 kg (6.43 moles) of tetrabutylammonium iodide. The suspension was stirred for 2 hrs., then 2.3 kg (12.86 moles) of cyclohexylmethyl bromide was added. The reaction mixture was refluxed for 36–48 hrs. After cooling the mixture, it was diluted with 3 L of water followed by 12 L of 3N hydrochloric acid and stirred for 2–6 hours. The organic phase was separated and discarded. The aqueous phase was washed four times with 3 L of methylene chloride, then basified with 2.5 L of 0.5N ammonium hydroxide solution. The racemic amine was extracted three times with 4 L of methylene chloride, dried over sodium sulfate and concentrated to dryness. The oil product was stirred with 2 L of hexane, filtered and concentrated to yield 1.14 kg (43.5%) of 1-(R,S)-(2-pyridyl)-2-cyclohexylethylamine.

EXAMPLE 3

To 465 g (4.3 moles) of 2-(aminomethyl) pyridine was added with stirring 456 g (4.3 moles) of benzaldehyde. The temperature was increased to 70°–80° C. The mixture was diluted with 2 L of MTBE and the water was removed by stirring the solution with 200 g of sodium sulfate overnight. The mixture was filtered and washed with 2 L of MTBE. To remove the remaining water, 100 g of molecular sieves were added. To the mixture was added 483 g (4.3 moles) potassium t-butoxide in portions followed by 842 g (4.38 moles) of cyclohexylmethyl methanesulfonate. After 10–20 hours, the mixture was hydrolyzed by the addition of 5 L water containing 720 mL of hydrochloric acid. The organic phase was separated and discarded. The aqueous phase was washed with 0.5 L of methylene chloride and basified with 0.5 L of ammonium hydroxide. The product was extracted with petroleum ether to yield 452 g of crude mine. The amine was purified by vacuum distillation at 88° C. and 0.5 Torr to give 353 g (35%) of 1-(R,S)-(2-pyridyl)-2-cyclohexylethylamine.

EXAMPLE 4

To a mixture of 21.6 g (0.2 mole) of 2-(aminomethyl) pyridine and 36.4 g (0.2 mole) benzophenone in 100 ml toluene was added 5.68 g (0.02 mole) of titanium (IV) isopropoxide and then it was heated to reflux using a water separator (Dean Stark distilling receiver) for 2–4 hours. Alter the theoretical amount of water was separated, the mixture was cooled and 16 g (0.4 mole) of sodium hydroxide followed by 36.9 g (0.1 mole) of tetrabutylammonium iodide and 35.4 g (0.2 mole) cyclohexylmethyl bromide was added. The mixture was heated to reflux for 12–18 hours. Then the mixture was poured with stirring into 300 ml of water containing 100 ml of concentrated hydrochloric acid. The mixture was stirred at 30°–50° C. for one to two hours, cooled and the organic phase separated and discarded. The aqueous phase was basified by the addition of 200 ml of ammonium hydroxide. The product was extracted with 100 ml of hexane three times, dried over anhydrous magnesium sulfate, filtered and concentrated to yield 37 g (90%) of 1-(R,S)-(2-pyridyl)-2-cyclohexylethylamine.

EXAMPLE 5

A mixture of 2.16 g of 2-picolylamine (20 mmoles) and 2.12 g of benzaldehyde (20 mmoles) was stirred for 5–20 hours. The reaction mixture was diluted with 20 ml of toluene with stirring, then 1.12 g (20 mmoles) of potassium hydroxide added followed by the addition of 3.7 g of tetrabutylammonium iodide (10 mmoles) and 3.55 g of cyclohexylmethyl bromide (20 mmoles). The mixture was refluxed for 6–24 hours, then cooled and stirred with 10 ml of a 2N HCl for 2–6 hours. The organic phase was discarded, the aqueous acidic phase was washed with methylene chloride. The aqueous phase was basified with ammonium hydroxide and the racemic amine extracted with methylene chloride to yield 45%–55% racemic 1-(2-pyridyl)-2-cyclohexylethylamine as a light yellow oil.

EXAMPLE 6

Resolution of
1-(2-pyridyl)-2-cyclohexylethylamine(+)-BCSA salt

To a solution of 1.176 kg (5.756 mole) of 1-(S,R)-(2-pyridyl)-2-cyclohexylethylamine and 6 L of ethyl acetate was added a suspension of 5.752 mole (+)-BCSA with stirring. The mixture was stirred overnight, filtered and washed with 1 L of ethyl acetate and washed twice with 0.5 L of ethyl acetate. The white crystals (1.22 kg) were dissolved in 12 L of 2-propanol at 75° C. and cooled to ambient temperature overnight. The clear supernatant was decanted off and the remaining crystals dissolved in 8 L of hot 2-propanol. The solution was filtered hot and allowed to cool to ambient temperature overnight. The crystals were filtered and washed with 1.5 L of 2-propanol and dried under vacuum to yield 726 g of white crystalline product (HPLC: 99% pure).

The original 2-propanol filtrate (12 L) was concentrated to 6 L, the resulting suspension was heated to 80° C. and the clear solution was allowed to cool overnight to ambient temperature. The crystals were filtered and combined with the above 9.5 L of 2-propanol filtrate and washings and dissolved at 80° C. The clear solution was allowed to cool overnight to ambient temperature. The crystals were collected and dried under vacuum to give 294 g (91% pure by HPLC). The crystals were dissolved in 3 L of hot 2-propanol, allowed to ambient temperature, filtered and washed with 0.5 L 2-propanol to give 246 g (HPLC: 99.3% pure) of white crystals.

EXAMPLE 6A

Recovering of (+)-S-1-(2-pyridyl)-2-cyclohexylethyl amine from amine(+)-BCSA salt The combined crystals of (+)-BCSA salt [726 g (HPLC: 99% pure) plus 246 g (HPLC: 99.3% pure)] were suspended in 5 L of water. To this suspension was added 0.5 L of ammonium hydroxide and the alkaline mixture was stirred for 2 hours. The (+)-S-1-(2-pyridyl)-2-cyclohexylethyl amine was extracted with 4 L methylene chloride and then extracted four times with 1 L of methylene chloride. The methylene chloride phase was dried over magnesium sulfate (anhydrous) and concentrated to dryness to give 403 g of (+)-S-1-(2-pyridyl)-2-cyclohexylethylamine (34.2% recovery based on racemic amine).

EXAMPLE 6A

Recovering of
(−)-R-1-(2-pyridyl)cyclohexylethylamine from amine(+)-BCSA salt

The original ethyl acetate filtrate and all 2-propanol mother liquors from the resolution of Example 6 were combined and concentrated to an oil. The oily residue was stirred with 14 L of water and 500 ml of amonium hydroxide, The enriched (−)-R-1-(2-pyridyl)-2-cyclohexylethylamine mixture was extracted four times with 1 L of methylene chloride, The methylene chloride extracts were dried over anhydrous magnesium sulfate and concentrated to dryness to give 864 g of (not completely dry) mostly (R)-(−)-amine (HPLC Ratio S/R=25:75).

EXAMPLE 7

1-(S)-2-pyridyl)-2-cyclohexylethylamine

The (+)-BCSA used in this example was prepared from [(1R)-(endo, anti)]-(+)-3-bromocamphor-8-sulfonic acid ammonium salt by treating an aqueous solution of the (+)-BCSA salt with Dowex 50×4H$^+$ ion-exchange resin.

Using the procedure of Example 6, 3.389 mole of (+)BCSA was added to a solution of 1.378 kg (6.745 mole) of racemic amine in 7 L of ethyl acetate. The resulting crystals of 1-(2-pyridyl)-2-cyclohexylethylamine-BCSA salt were collected and washed with ethyl acetate to give 1.364 kg S-enriched S:R ratio=78:22 (by HPLC). The ethyl acetate supernatant containing the R-enantiomer as the major product, was heated and refluxed with 3.7 mole of HCl gas and 206 g of salicylaldehyde for 24–36 hours. The mixture was cooled and stirred with 4 L of water and 0.3 L of concentrated hydrochloric acid. The aqueous phase was separated, washed with ethyl acetate, and basified with ammonium hydroxide. The racemic amine was extracted with methylene chloride, dried and concentrated. The oil product was dissolved in 2.5 L of ethyl acetate and treated with 1.695 mole of (+)BCSA. The crystals were collected and washed with ethyl acetate to give an additional 540 g of S-enriched amine. Repeating the above sequence several times, resulted in approximately 2.4 kg of S-enriched amine (75–85% S-enantiomer).

EXAMPLE 8

Preparation of (+)-BCSA from
(+)-BCSA-Ammonium Salt

Various commercial methods exist for the preparation (+)- or (−)-3-bromocamphor-8-sulfonic acid from the ammonium salt or the calcium salt.

Applicants in the present invention have developed a novel process for the preparation which (+)-3-bromocamphor sulfonic acid which is less expensive and time consuming than previously known commercial methods. A suspension of 311 g (0.95 mole) of [(1R)-(endo,anti)]-(+)-

3-bromocamphor-8-sulfonic acid ammonium salt (CAS [14575-84-9]) in 500 ml water was added to 74.09 g (0.475 mole) of calcium hydroxide. The mixture was stirred at room temperature for 6–24 hours, then the solution was concentrated to a syrup. The resulting neutral solution of (+)-BCSA calcium salt was diluted with 0.5 L of water and treated with 46.6 g (0.475 mole) of sulfuric acid. The calcium sulfate was filtered off and the clear filtrate concentrated to a syrup and used without further purification in applicants' novel process as a source of the (+)-3-bromocamphor sulfonic acid. The inorganic salt used is either the ammonium salt or the calcium salt, the ammonium salt being preferred.

This same procedure is used to prepare [(1S)-(endo,anti)]-(−)-3-bromocamphor-8-sulfonic acid (CAS [55870-50-3]) in the same quantities. Applicants' novel process of preparing pure enantiomers of 2-pyridyl-2-cyclohexylethylamine from a racemic mixture (R:S ratio 1:1) is only by way of example because the separation procedures of the process are equally applicable to mixtures in which R:S ratios vary over a large range. For example, pure enantiomers (99% pure) can be recovered from racemic mixtures in any R:S proportions. (Eg. 70:30 or 30:70 R:S ratios.)

EXAMPLE 9

Fractional Crystallization of S-enriched Amine

The enriched S-amine of Example 7 (S-enantiomer= 75–85%, R-enantiomer=25–15%) and 23 L of 2-propanol were heated to reflux until a clear solution resulted. The solution was allowed to cool to room temperature. The supernatant was drained and the remaining crystals were recrystallized three times from 2-propanol to give +99% S-amine. The supernatants of the fractional crystallization were recrystallized from 2-propanol until a purity of 99% of S-amine was obtained. The filtrates containing <50% S-enantiomer are racemized in ethyl acetate as the (+) BCSA-salt in the presence of salicylaldehyde. After cooling, S-enriched amine is collected by filtration. In the presence of (+) BCSA, using this crystallization-induced asymmetric transformation, the S-amine (+) BCSA-salt is essentially removed from the system by virtue of its insolubility driving equilibrium (see J. Jacques, A. Collet, S. Wilen in Enantiomers, Racemates and Resolution; Wiley: N.Y. 1981; pp 369–377). All >99% (+) BCSA S-amine salt fraction were combined and suspended in 10 L of water and basified with 0.7 L of ammonium hydroxide to pH 9–10. The free pure S-amine was extracted with methylene chloride, washed with water, dried over sodium sulfate, filtered and concentrated to yield 697 g (45%) 1-(S)-(2-pyridyl)-2-cyclohexylethylamine. From the aqueous phase, the (+) BCSA ammonium chloride salt is recovered by concentration in 88%–100% yield.

EXAMPLE 10

[(2-Cyclohexyl-1-(2-pyridyl)ethylamino]-5-methylbenzoxazole

To a solution of 132.8 g (0.65 moles) 1-(+)-(S)-(2-pyridyl)-2-cyclohexylethylamine in 550 mL methylene chloride was added 109 g (0.65 moles) 2-chloro-5-methylbenzoxazole followed by 168 g (1.3 moles) diisopropylethylamine. The reaction mixture was heated to reflux for 5–40 hours, cooled and concentrated under reduced pressure. The mixture was dissolved in 2 L of ethanol. Addition of 2–3 L of water gave crude [(2-cyclohexyl-1-(2-pyridyl)ethylamino]-5-methylbenzoxazole. Recrystallization from ethanol/water gave 190 g (83%) as a hydrate; mp 80°–86° C.

Separation of the desired S or R enantiomer by the novel process of the present invention results in the recovery of pure or substantially pure enantiomers/isomers while avoiding the necessity of protecting the amine group which require extra stages, expensive and/or hazardous materials and the use of chromatography for purification.

While the present invention has been described with regard to a preferred embodiment thereof, the description is for illustrative purposes only and is not to be construed as limiting the scope of the invention. Various modifications and changes may be made by those skilled in the art without departing from the true spirit and scope of the invention as defined by the appended claims.

What is claimed is:

1. A process for producing (+)-S or (−)-R-1-(2-pyridyl)-2-cyclohexylethylamine which comprises admixing 1-(S, R)-(2-pyridyl)-2-cyclohexylethylamine with (+)- or (−)-3-bromocamphor-8-sulfonic acid to produce a crystalline addition product, and admixing a solution of an alkali metal hydroxide or ammonium hydroxide with the crystalline addition product to produce (+)-S or (−)-R-1-(2-pyridyl)-2-cyclohexylethylamine.

2. The process of claim 1 in which (+)-S-1-(2-pyridyl)-2-cyclohexylethylamine is produced.

* * * * *